(12) United States Patent
Gong et al.

(10) Patent No.: US 8,632,837 B2
(45) Date of Patent: Jan. 21, 2014

(54) DIRECT FLUID COATING OF DRUG ELUTING BALLOON

(75) Inventors: Victoria M. Gong, Sunnyvale, CA (US); Stephen D. Pacetti, San Jose, CA (US); Anthony S. Andreacchi, San Jose, CA (US); Shih-hsiung Albert Yuan, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 255 days.

(21) Appl. No.: 13/108,283

(22) Filed: May 16, 2011

(65) Prior Publication Data

US 2011/0281019 A1 Nov. 17, 2011

Related U.S. Application Data

(60) Provisional application No. 61/345,575, filed on May 17, 2010.

(51) Int. Cl.
*B03D 3/02* (2006.01)
*A61M 25/10* (2013.01)
*B05B 7/16* (2006.01)

(52) U.S. Cl.
USPC ....... 427/2.1; 427/2.28; 427/372.2; 427/2.24; 118/58; 118/300

(58) Field of Classification Search
USPC .................... 427/2.1, 2.24, 2.28; 118/58, 300
See application file for complete search history.

(56) References Cited

U.S. PATENT DOCUMENTS

| | | |
|---|---|---|
| 4,748,982 A | 6/1988 | Horzewski et al. |
| 5,300,085 A | 4/1994 | Yock |
| 5,370,614 A | 12/1994 | Amundson et al. |
| 5,464,650 A | 11/1995 | Berg et al. |
| 5,496,346 A | 3/1996 | Horzewski et al. |
| 5,591,227 A | 1/1997 | Dinh et al. |
| 5,626,600 A | 5/1997 | Horzewski et al. |
| 5,649,977 A | 7/1997 | Campbell |
| 5,911,452 A | 6/1999 | Yan |
| 6,120,847 A | 9/2000 | Yang et al. |
| 6,406,457 B1 | 6/2002 | Wang et al. |
| 6,478,807 B1 | 11/2002 | Foreman et al. |
| 6,494,906 B1 | 12/2002 | Owens |
| 6,669,980 B2 | 12/2003 | Hansen |
| 6,676,987 B2 * | 1/2004 | Zhong et al. .................. 427/2.24 |

(Continued)

OTHER PUBLICATIONS

U.S. Appl. No. 61/345,569, filed May 17, 2010, Pacetti et al.

(Continued)

*Primary Examiner* — Cachet Sellman
(74) *Attorney, Agent, or Firm* — Baker Botts L.L.P.

(57) ABSTRACT

A system and method for coating an expandable member of a medical device comprises providing a dispenser in fluid communication with a fluid source with the dispenser having at least one outlet to dispense fluid of the fluid source therefrom. The outlet(s) of the dispenser is positioned proximate a surface of an expandable member, with relative movement between the outlet(s) and the surface of the expandable member established along a coating path, and fluid is dispensed from the dispenser to form a substantially continuous bead of fluid between the at least one outlet and the surface of the expandable member along the coating path, and simultaneously drying the fluid while dispensing the fluid from the dispenser to control flow of fluid on the surface of the expandable member. The fluid source can include a variety of therapeutic agents.

20 Claims, 5 Drawing Sheets

(56) References Cited

U.S. PATENT DOCUMENTS

| | | | |
|---|---|---|---|
| 6,743,462 B1* | 6/2004 | Pacetti | 427/2.24 |
| 7,241,344 B2 | 7/2007 | Worsham et al. | |
| 7,335,227 B2 | 2/2008 | Jalisi | |
| 7,378,105 B2 | 5/2008 | Burke et al. | |
| 7,445,792 B2 | 11/2008 | Toner et al. | |
| 7,455,876 B2 | 11/2008 | Castro et al. | |
| 7,504,125 B1* | 3/2009 | Pacetti et al. | 427/2.24 |
| 7,524,527 B2 | 4/2009 | Stenzel | |
| 2004/0234748 A1 | 11/2004 | Stenzel | |
| 2005/0196518 A1* | 9/2005 | Stenzel | 427/2.1 |
| 2007/0031611 A1* | 2/2007 | Babaev | 427/600 |
| 2007/0088255 A1 | 4/2007 | Toner et al. | |
| 2008/0113081 A1 | 5/2008 | Hossainy et al. | |
| 2009/0226598 A1* | 9/2009 | Feng et al. | 427/2.1 |
| 2010/0023108 A1 | 1/2010 | Toner et al. | |
| 2010/0030183 A1 | 2/2010 | Toner et al. | |
| 2010/0055294 A1 | 3/2010 | Wang et al. | |
| 2011/0281020 A1 | 11/2011 | Gong et al. | |
| 2012/0022540 A1 | 1/2012 | Chasmawala et al. | |
| 2012/0064223 A1 | 3/2012 | Gamez et al. | |
| 2012/0065583 A1 | 3/2012 | Serna et al. | |
| 2012/0128863 A1 | 5/2012 | Nguyen et al. | |
| 2012/0143054 A1 | 6/2012 | Eaton et al. | |
| 2012/0315374 A1 | 12/2012 | Nguyen et al. | |
| 2012/0315375 A1 | 12/2012 | Shen et al. | |
| 2012/0315376 A1 | 12/2012 | Nguyen et al. | |

OTHER PUBLICATIONS

Unverdorben, Martin, "The Paclitaxel-Eluting PTCA-Balloon Catheter in Coronary Artery Disease PEPCAD I-SVD PEPCAD II-ISR", Clinical Research Institute, Center for Cardiovascular Diseases, 2005-2006, Rotenburg/Fulda, Germany.

U.S. Appl. No. 12/882,953, filed Jan. 15, 2013 Non-Final Office Action.

U.S. Appl. No. 12/882,990, filed Dec. 6, 2012 Non-Final Office Action.

U.S. Appl. No. 12/882,990, filed Apr. 8, 2013 Response to Non-Final Office Action.

U.S. Appl. No. 12/882,953, filed Apr. 12, 2013 Response to Non-Final Office Action.

U.S. Appl. No. 13/280,067, filed Apr. 26, 2013 Applicant Summary of Interview with Examiner.

U.S. Appl. No. 13/158,101, filed Apr. 26, 2013 Restriction Requirement.

U.S. Appl. No. 13/109,156, filed Apr. 26, 2013 Restriction Requirement.

U.S. Appl. No. 13/158,057, filed Apr. 26, 2013 Restriction Requirement.

* cited by examiner

DIRECT FLUID COATING OF DRUG ELUTING BALLOON

CROSS-REFERENCE TO RELATED APPLICATION

This application claims priority to U.S. Provisional Application No. 61/345,575 entitled "Direct fluid coating of drug eluting balloon," filed May 17, 2010 which is incorporated herein by reference in its entirety.

BACKGROUND OF THE DISCLOSED SUBJECT MATTER

1. Field of the Disclosed Subject Matter

The presently disclosed subject matter is related to the delivery of therapeutic agents from an interventional medical device. More particularly, the presently disclosed subject matter relates to an interventional device for delivery of therapeutic agents from an expandable member, such as a balloon. The disclosed subject matter also relates to a method and apparatus for applying one or more therapeutic agents onto the expandable member as well as the assembly of the medical device.

2. Description of Related Subject Matter

Atherosclerosis is a syndrome affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. Dissection, or perforation, of the blood vessel is another complication of angioplasty that can be improved by stenting. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227, 7,378,105; 7,445,792; 7,335,227, each of which are hereby incorporated by reference in their entirety. However, a drawback of drug eluting stents is a condition known as late stent thrombosis. This is an event where a blood clot forms inside the stent, which can occlude blood flow.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stent, the patients treated with drug coated balloons experienced only 3.7 percent restenosis and 4.8% MACE (material adverse coronary events) as compared to patients treated with drug eluting stents, in which restenosis was 20.8 percent and 22.0 percent MACE rate. (See, PEPCAD II study, Rotenburg, Germany).

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time may be longer for a peripheral procedure, however typically even for peripheral procedures the balloon is expanded for less than 5 minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent.

Furthermore, conventional techniques for applying a coating, such as a therapeutic agent, may not be desirable for coating balloons, or other expandable members of medical devices. Such convention techniques include spraying (air-atomization, ultrasonic, electrostatic, etc.), dip-coating, spin-coating, vapor deposition, roll coating, micro-droplet coating, etc. Balloons present a cylindrical surface to be coated where it is desired to uniformly coat only the working length of the balloon and no other portion of the balloon or catheter. Many of these conventional techniques do not provide sufficient coating uniformity or edge control. Moreover, many of these techniques are not efficient in their utilization of the therapeutic agent that can be costly. For example, with the spray coating techniques commonly used to coat drug eluting stents, only a fraction of the therapeutic agent discharged is retained on the surface of the medical device. This inefficiency is exacerbated with medical devices having larger surface areas, such as peripheral balloons, wherein the amount of therapeutic agent retained on the device can be as low as 2% of the amount of therapeutic agent discharged.

Thus there remains a need, and an aim of the disclosed subject matter is directed towards, the application of one or more therapeutic agents to the surface of an expandable member of a medical device.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system and method of coating an expandable member of a medical device. The method comprises providing a dispenser in fluid communication with a fluid source containing at least one therapeutic agent, with the dispenser having at least one outlet to dispense fluid of the fluid source, and positioning the at least one outlet of the dispenser in proximity to a surface of an expandable member. Relative movement is established between the at least one outlet and the surface of the expandable member along a coating path, and fluid is dispensed from the dispenser to form a substantially continuous bead of fluid between the outlet(s) and the surface of the expandable member along the coating path, and simultaneously drying the fluid while dispensing the fluid from the dispenser to control flow of fluid on the surface of the expandable member.

The relative movement includes rotation, translation, or a combination thereof about at least one axis, of at least one of the expandable members and the at least one outlet. Additionally, the relative movement can further include rotation, axial translation, or a combination thereof, of the other of the expandable member and the at least one outlet. For example, the relative movement can define a helical path of the outlet with respect to the expandable member, and/or the expandable member is moved along a first axis, and the outlet can be moved along a second axis transverse to the first axis.

The dispensing of fluid to the surface of the expandable member can be repeated along a plurality of coating paths. Additionally, or alternatively, a first fluid can be dispensed during a first coating path, and a second fluid can be dispensed during a second coating path. Additionally, the method can include drying the fluid on the surface between successive coating paths. The drying of the fluid on the surface can occur at specific periods before and after dispensing or simultaneously with the dispensing of the fluid along the coating path. The dispensing of fluid can be controlled to apply a substantially uniform or non-uniform coating of fluid to a predetermined area of the expandable member. The method also includes at least partially expanding the expandable member prior to dispensing fluid to the surface of the expandable member.

The dispenser is selected from the group including pipet tubing, flexible tubing, coaxial tubing, hypotubes, dies, ball-bearing dispense tubing, syringe, needles, and other non-contacting applicators capable of forming a continuous bead. Additionally, the dispenser can include a plurality of outlets arranged along a common axis, angularly offset form each other, or combinations thereof. Each dispenser outlet can be in communication with a different fluid source, and can be heated during the dispensing operation.

The disclosed subject matter also includes a system for coating an expandable member of a medical device. The system includes a support structure to support an expandable member of a medical device, and a dispenser in fluid communication with a fluid source and having at least one outlet for dispensing fluid of the fluid source therefrom, wherein the dispenser can be positioned with the at least one outlet proximate a surface of an expandable member supported by the support structure. A dryer is provided proximate the dispenser to simultaneously dry the fluid while dispensing the fluid from the dispenser to control flow of fluid on the surface of the expandable member. A drive assembly is employed to establish relative movement between the at least one outlet and the surface of the expandable member to dispense fluid from the dispenser as a substantially continuous bead between the at least one outlet and the surface of the expandable member along a coating path.

The dispenser is capable of varying the rate in which fluid is dispensed from the at least one outlet. Additionally, the drive assembly is capable of varying the speed of relative movement between the at least one outlet and the surface of the expandable member, as well as establishing a plurality of coating paths for delivery of fluid from the dispenser to the surface of the expandable member. A dryer can be provided to apply heat, forced gas, cold temperature, vacuum, infra-red energy, microwave energy, or a combination thereof to the surface of the expandable member.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Reference will now be made in detail to embodiments of the disclosed subject matter, an example of which is illustrated in the accompanying drawing. The method and corresponding steps of the disclosed subject matter will be described in conjunction with the detailed description of the system.

The methods and systems presented herein can be used for applying one or more coatings to a medical device. The disclosed subject matter is particularly suited for directly applying therapeutic agents, and other fluid compounds, to select portions of an expandable member. While the disclosed subject matter references application of a fluid to an expandable member, it is to be understood that the methods and systems disclosed herein can also be employed to apply therapeutic, polymeric, or matrix coatings to various surfaces of medical devices, as so desired.

The disclosed subject matter provides a method, and corresponding system, to coat an expandable member, or select portions thereof, by a direct application process. The direct application process applies a coating without atomization, or the formation of droplets, of the coating fluid. Additionally, the disclosed subject matter provides a system and method for improved efficiency of the dispensing of a coating solution, which can be controlled based on the volume of coating solution dispensed, rather than via a weight based control. Indeed, the disclosed subject matter provides a system and method for dispensing of a coating solution which can achieve 95.0% or greater transfer efficiency, i.e., 95.0% of the coating solution dispensed is applied to the expandable member.

In accordance with the disclosed subject matter, a method of coating an expandable member of a medical device comprises providing a dispenser in fluid communication with a fluid source with the dispenser having at least one outlet to dispense fluid of the fluid source therefrom. The at least one outlet of the dispenser is positioned proximate a surface of an expandable member, with relative movement between the at least one outlet and the surface of the expandable member established along a coating path, and fluid is dispensed from the dispenser to form a substantially continuous bead of fluid between the outlet and the surface of the expandable member along the coating path.

Figure 1:
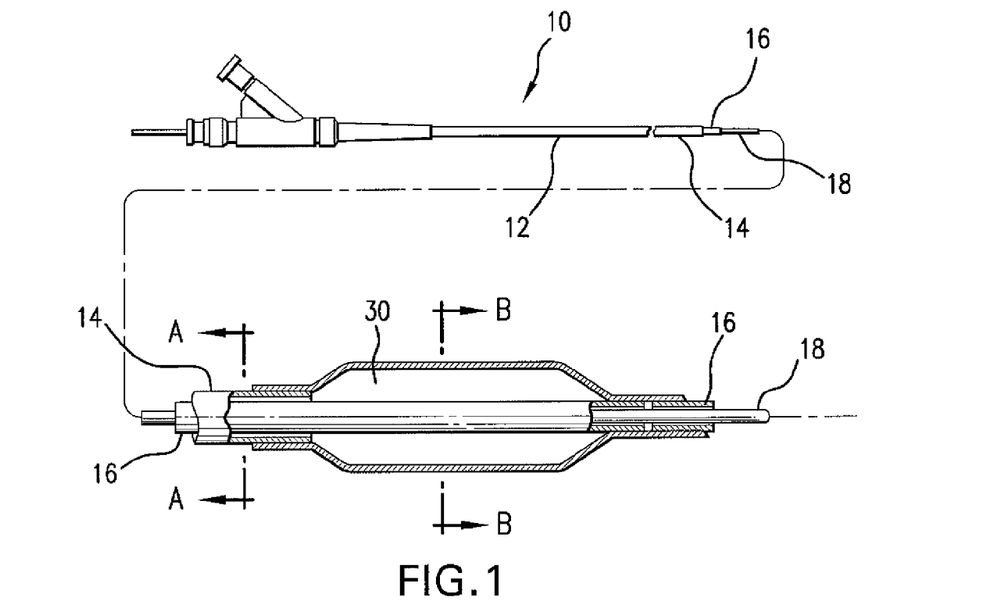
FIG. 1 is a schematic side view representative balloon catheter in accordance with the disclosed subject matter.
Figure 1A:
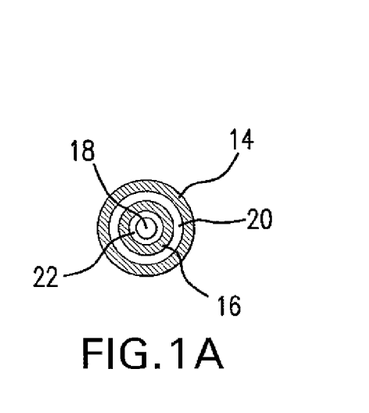
FIG. 1A is a cross-sectional view taken along lines A-A in FIG. 1.

For purpose of explanation and illustration, and not limitation, an exemplary embodiment of a medical device having an expandable member is shown schematically in FIGS. 1 and 1A. Particularly, and as illustrated, the medical device embodied herein is a balloon catheter 10, which includes an elongated catheter shaft 12 having a proximal end and having a distal end and an expandable member 30 located proximate the distal end of the catheter shaft. The expandable member, or balloon as depicted herein, has an outer surface and an inner surface disposed at the distal end portion of the catheter shaft. In accordance with the disclosed subject matter, a coating is applied to at least a portion of the outer surface of the balloon.

Figure 1B:
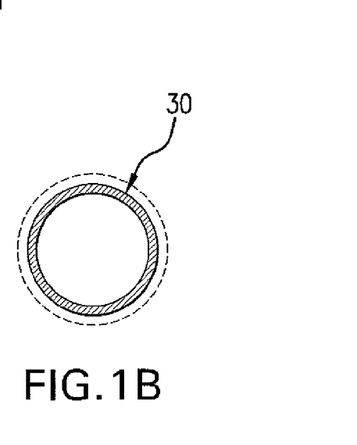
FIG. 1B is a cross-sectional view taken along fines B-B in FIG. 1.

The elongated catheter shaft 12 comprises an outer tubular member 14 and an inner tubular member 16. The outer tubular member 14 defines an inflation lumen 20 disposed between the proximal end portion and the distal end portion of the catheter shaft 12. Specifically, as illustrated in FIG. 1A, the coaxial relationship of this representative embodiment defines an annular inflation lumen 20 between the inner tubular member 16 and the outer tubular member 14. The expandable member 30 is in fluid communication with the inflation lumen 20. The inflation lumen can supply an inflation medium under positive pressure and can withdraw the inflation medium, i.e. provide negative pressure, from the expandable member. The expandable member 30 can thus be inflated and deflated. The elongated catheter is sized and configured for delivery through a tortuous anatomy, and can further include a guidewire lumen 22 that permits it to be delivered over a guidewire 18. As illustrated in FIG. 1A, the inner tubular member 16 defines the guidewire lumen 22 for the guidewire 18. Although FIGS. 1 and 1b illustrate the guidewire lumen as having an over-the-wire (OTW) construction, the guidewire lumen can be configured as a rapid-exchange (RX) construction, as is well known in the art.

A wide variety of balloon catheters and balloon constructs are known and suitable for use in accordance with the disclosed subject matter. For example, the expandable member can be made from polymeric material such as compliant, non-compliant or semi-compliant polymeric material or polymeric blends. Examples of such suitable materials include, but are not limited to, nylon 12, nylon 11, nylon 9, nylon 6, nylon 6/12, nylon 6/11, nylon 6/9, and nylon 6/6, polyurethane, silicone-polyurethane, polyesters, polyester copolymers, and polyethylene. Examples of other balloon and catheter embodiments which can be employed in accordance with the disclosed subject matter include U.S. Pat. Nos. 4,748,982; 5,496,346; 5,626,600; 5,300,085, 6,406,457 and U.S. application Ser. Nos. 12/371,426; 11/539,944; 12/371,422, each of which is hereby incorporated by reference in their entirety.

In one embodiment, the coating is applied to the expandable member of the fully assembled medical device. As described above with reference to FIGS. 1A-B, medical devices such as the catheter 10 include a plurality of components which are typically manufactured as separate discrete components and thereafter assembled together. Applying a coating to the expandable member at an upstream stage of an assembly line requires extensive measures to minimize or prevent the coating from being exposed to various equipment and processes during the downstream portion of the assembly line. Such exposure can render the coating prone to damage and/or contamination during final assembly of the catheter, and can result in scrapping of the entire catheter. In order to avoid such exposure and damage to the coating in conventional catheter assembly lines additional equipment including monitoring and safety controls would be required. Accordingly, applying the coating to the expandable member of a fully assembled catheter avoids the unnecessary complexity, and excessive costs associated with such a modified assembly line.

In accordance with the disclosed subject matter, any of a variety of fluid compositions can be applied to the expandable member. For example, the fluid can include a therapeutic agent for treatment of a disease state. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector. However, the therapeutic agents can include, cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel.

Additionally or alternatively, the fluid can include other compounds or additives, such as polymers, binding agents, plasticizers, solvents, surfactants, additives, chelators, fillers, and the like. Examples of possible compounds include 
zotarolimus, polyvinylpyrrolidone and glycerol. In one embodiment the therapeutic agent can be provided in liquid form or dissolved in a suitable solvent. In another embodiment, the therapeutic agent is provided as a particulate and mixed in a suitable carrier for application as a fluid.

Figure 2:
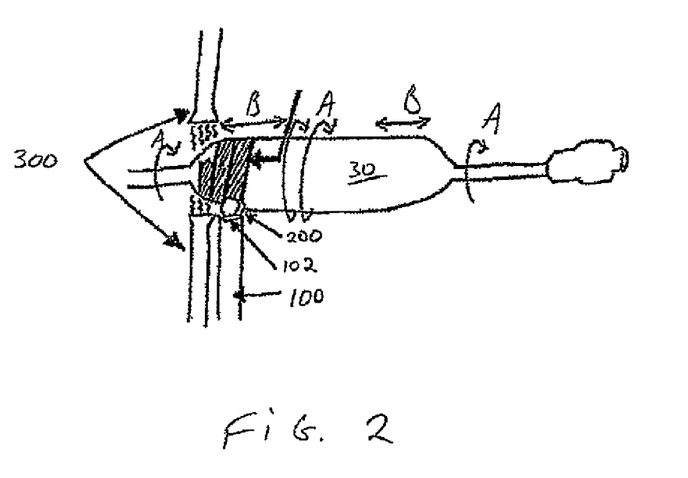
FIG. 2 is a schematic representative view of direct fluid coating in accordance with the disclosed subject matter.

An embodiment of the coating process and system of the disclosed subject matter is illustrated in FIG. 2 for purpose of explanation and not limitation. The dispenser depicted herein is shown as a pipet 100 having an outlet 102 positioned proximate expandable member 30 such that the fluid dispensed from the pipet is in continuous fluid contact with the expandable member 30 without atomization of the coating solution. As the coating solution is delivered from a fluid source, e.g. reservoir (not shown), through the dispenser outlet, a continuous fluid medium or bead 200 of solution directly contacts the surface of the expandable member.

A positive pressure is applied to assist with dispensing fluid from the outlet. Alternatively, the fluid can be dispensed from the outlet via capillary action only, i.e., the surface tension pulls the bead of coating solution 200 onto the surface of the expandable member. Furthermore, the outlet can be heated prior to and/or during the dispensing of the coating solution. The heating of the dispenser can reduce the viscosity of the coating solution and therefore accelerate the coating process as well as reduce the potential for clogging or occluding of the dispenser outlet 102. FIG. 2 depicts the outlet generally at a right angle to the balloon surface. However, alternative alignments and orientations can be used as desired or needed for the type and dimensions of expandable members.

Coating process and systems of the disclosed subject matter can be performed with the expandable member in a fully or partially inflated condition, as well as in a deflated condition. When deflated, the expandable member can be pleated, folded, wrinkled or pressed. In the embodiment illustrated in FIG. 2, the expandable member is fully inflated to allow coating of all or select portions of the outer surface.

As the fluid is delivered from the fluid source to the outlet 102 of the dispenser in the form of a continuous bead, relative movement is established between the outlet 102 and the expandable member 30 to effect a uniform, or non-uniform, coating path as desired. For example, and as depicted in FIG. 2, the coating path can define a continuous spiral or helical pattern along the outer surface of the expandable member. Alternatively, coating paths can be established such as discrete circumferential rings, discrete lines extending along the expandable members longitudinal axis, and combinations thereof. Hence, the relative movement can include rotation, translation, or combinations thereof, of either, or both, the expandable member 30 and the outlet 102.

For example, the expandable member can be rotated about its central axis, as shown by arrows A in FIG. 2, and simultaneously translated along the central axis, as shown by arrow B in FIG. 2. Additionally, or alternatively the expandable member 30 can rotate relative a first axis, and the outlet 102 translate relative a second axis, e.g., to define a helical coating path. Accordingly, any number of coating paths can be selected and provided on the expandable member. The various movements described herein can be performed simultaneously, sequentially, continuously or intermittently, as so desired.

Movement of the medical device and/or the outlet of the dispenser is accomplished by providing a support assembly. The support assembly can maintain the position of one element, e.g. the dispenser, while allowing movement of the other element, e.g., the medical device. Alternatively, the support assembly can allow movement of both elements. Movement can be performed manually, or by providing a drive assembly with suitable drive source, such as a motor or the like, and appropriate controller as know in the art.

Simultaneous with the relative movement, the fluid is dispensed from the outlet to form a continuous bead between the outlet and the surface of the expandable member along the coating path. Generally, it has been determined that the formation and maintenance of the continuous bead of fluid will be a function of the fluid density, and average velocity of the fluid from the outlet. In one embodiment, the Reynolds number, i.e. ratio of momentum or inertial force to viscosity, for the flow out of the outlet is less than 2300 such that the flow remains substantially laminar. The Reynolds number being defined by the equation $Re=(\rho *v*l)/\mu$, wherein "l" is a dimension of the outlet. Additionally, the average volumetric flow rate of the fluid exiting the outlet lies within the range of 3-110 µl/min. It therefore is possible to form a substantially continuous bead by controlling one or more of these variables. For example, the average velocity of the fluid can exit in the range of approximately 0.0411 to 4.11 cm/sec.

In one embodiment, the bead 200 diameter was maintained at a predetermined size of at least 0.03 in. Alternatively, bead diameters of between 0.8 mm (or 0.03 in) and 2.5 mm (~0.1 in) for tubing inner diameters between 0.006 inch to 0.20 inch are considered to be within the scope of the disclosed subject matter. In another embodiment, a 3.0 mm×18 mm Pebax expandable member was rotated at 100 rpm, and translated at a linear speed of 1.0 mm/sec which resulted in approximately 650 μg/pass of a coating solution applied to the expandable member. The cycle time for applying a coating to an expandable member can vary depending on the size of the expandable member, the flow rate of the coating fluid, and the speed of relative movement, with a typical cycle time lasting from about 1 to 15 minutes. The rotational movement of the expandable member provides an additional advantage of distributing the coating solution around the circumference of the expandable member and preventing any accumulation on the downward side due to gravity induced flow. Additionally, or alternatively, as described further below, the applied bead is dried to control and/or prevent a flow of the fluid on the surface of the expandable member. To create the relative movement between the expandable member and dispenser, the expandable member was positioned on a motorized mandrel geared to rotate and/or translate as well as provide inflation/deflation of the expandable member.

In accordance with another aspect of the disclosed subject matter, the speed at which the expandable member and/or outlet is moved can be varied to a variety of coating properties including thickness, width and volume of the coating. For example, a slower speed of relative movement between the elements will result in greater volume of fluid per pass. Similarly, the rate in which fluid is dispensed from the outlet also can be controlled to adjust or control the coating properties applied to the surface of the expandable member. That is, a greater rate of fluid dispensed will result in a greater volume per pass if the speed of relative movement is maintained constant. Hence, any number of coating patterns and properties can be achieved by the disclosed method and system.

The desired portions of the expandable member can be coated with a single pass or cycle of relative movement between the expandable member and dispenser. Alternatively, a plurality of passes or cycles of coating operation discussed above can be performed. Such multiple passes or cycles allows for further variation in the coating properties along the expandable member length. For example, one portion of the expandable member can be coated with a different number of coating layers of fluid than another portion of the expandable member thereby creating a gradient of the coating solution on the expandable member. Further, the methods and apparatus of the disclosed subject matter can be employed to apply layers of different coating compositions to the expandable member. For example, therapeutic-free primers, concentrated therapeutic layers, and drug-excipient layers can be applied. As discussed above, varied coating properties allow for greater flexibility and customization of the catheter to provide a greater range of applications and ability to meet patient needs.

Figure 3:
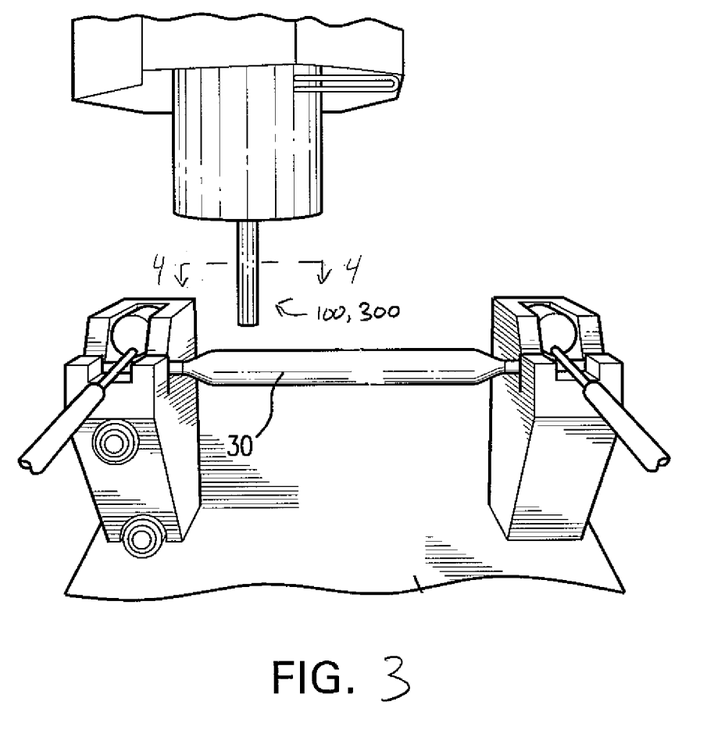
FIG. 3 is a schematic representation of a dispenser and drying apparatus in accordance with the disclosed subject matter.
Figure 4:
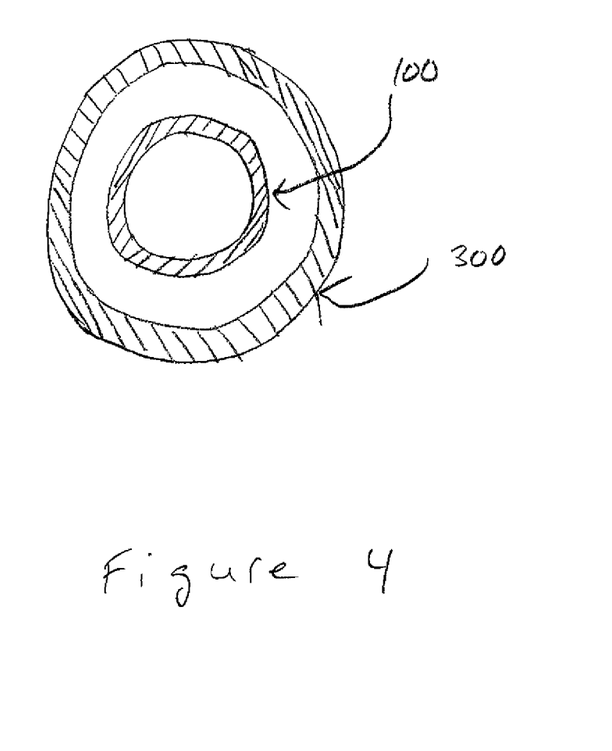
FIG. 4 is a schematic cross-sectional view of the dispenser and drying apparatus of FIG. 3.

In accordance with another aspect of the disclosed subject matter, a drying apparatus can be employed to control or prevent the flow of fluid applied on the surface of the expandable member and to accelerate the coating process. As shown in FIG. 2, a dryer 300 can be positioned downstream of the dispenser to apply heat, forced gas, cooled gas, vacuum, infra-red energy, microwave energy, or a combination thereof to the surface of the expandable member. Additionally, or alternatively, the drying nozzle 300 can be collinear or coaxial with the dispenser 100 by either circumscribing the outlet 102 or otherwise surround the outlet as with an annular opening, as shown in FIGS. 3-4. For example, the drying operation can employ air, or ambient nitrogen, in a drying nozzle of 0.081 in, at a pressure of 5 to 25 psi, and a flow rate of about 100-700 ml/min. As embodied herein, the flow rate can be calculated to equation: flow rate=(26.86*Pressure)+4.5204. Further, applying a drying gas simultaneously, e.g. air or ambient nitrogen at 10 psi, evaporates solvents contained in the fluid and facilitates drying of the coating such that the coating disposed on the expandable member does not flow. In some embodiments, a drying operation can be conducted between successive coating passes or cycles. Additionally, or alternatively, the drying operation can be conducted concurrently with a coating pass or cycle, as depicted in FIG. 2. Similar to the dispenser 100 discussed above, the drying apparatus 300 can be oriented at any angle between 0°-90° with respect to the expandable member, and be configured for relative movement.

While the dispenser of the embodiment illustrated in FIG. 2 depicts a dispenser configured as a pipet, additional or alternative dispensers can be employed. Some examples of such dispensers include flexible tubing, coaxial tubing, hypotubes, dies, ball-bearing dispense tubing, syringe, needles, and other non-contacting applicators that are capable of forming a continuous bead. Furthermore, FIG. 2 depicts a dispenser having a single outlet 102 perpendicular to the expandable member though alternative angles between 0°-90° can be employed. Also, the use of a plurality of outlets can be employed. Each outlet can be oriented perpendicular, disposed adjacent each other along the axis of the expandable member, and/or spaced circumferentially about the expandable member.

In this regard, a plurality of reservoirs containing distinct coating solutions can be provided with each dispenser in fluid communication with a separate reservoir. As with the outlet of FIG. 2, the dispensers can be positioned at various locations and orientations relative to the expandable member. Additionally, the expandable member 30 can be oriented in a generally horizontal position, as shown in FIG. 2, vertically, or at or at any angle between 0°-90°, if desired. Orienting the expandable member in a vertical configuration can be advantageous in larger size expandable members, e.g. peripheral balloons, since the gravitational force acts parallel the expandable member's longitudinal axis thereby preventing deformation such as arching or bowing of the expandable member and associated catheter shaft, which the expandable member can be susceptible to when in the horizontal position.

In accordance with another aspect of the disclosed subject matter, the outlet of the dispenser is maintained at a predetermined or fixed distance from the expandable member surface. Maintaining a fixed distance between the dispenser outlet and the expandable member, in combination with uniform rotation and translation as discussed above, provides greater control over the coating pattern to be applied to the expandable member surface. Such control can be advantageous by providing a consistent dosage of the therapeutic agent along the portion of the expandable member.

Additionally, maintaining a fixed distance between the dispenser outlet and the expandable member surface assists in maintaining a continuous bead of fluid from the outlet. For example, discrete droplets of fluid could form if the distance between the outlet and the surface of the expandable member were too great. Conversely, if the distance between the dispenser outlet and the expandable member surface were too small, undesired or accidental contact between the outlet and expandable member surface can occur resulting in tearing or scratching of the expandable member surface or abrasion to the coating applied to the expandable member. The distance between the outlet and the surface of the expandable member can depend upon a number of variables, including viscosity of the fluid, surface tension of the fluid, pump rate of the fluid, diameter of the dispenser exit orifice, volatility of the solvents in the fluid, speed at which the fluid is dispensed and/or size of the outlet opening. For example, when using a pipet type dispenser, the distance between the outlet and the surface generally should be less than 40 times the smallest cross dimension of the outlet.

The fixed distance between the outlet and the surface of the expandable member can be monitored in a number of ways in accordance with the disclosed subject matter. Particularly, the fixed distance can be monitored by displacing the outlet to track the surface, or by controlling displacement of the surface of the expandable member relative to the outlet. Examples of suitable methods and systems are disclosed in U.S. Patent Application Ser. No. 61/345,569, which is hereby incorporated by reference in its entirety.

As discussed above, the coating method and system of the disclosed subject matter can be performed on a previously assembled medical device, e.g. balloon catheters. Often the force required to rotate or otherwise move the expandable member is applied to a location, and/or component, proximal of the expandable member. Therefore, significant force may be required to overcome the friction and inertia of the various components of the medical device in order to achieve movement of the expandable member. Thus, any reduction or minimization of points of contact between the encasement and expandable member is advantageous as the frictional forces generated during the relative movement will in turn be minimized, thereby reducing the amount of force required by the support assembly, or manual operator, to establish relative movement. As the proximal components of medical device are often polymeric and not torsionally rigid, undue friction on the expandable member can lead to torsional loading and unloading of the proximal members. This leads to inconsistent rotation of the medical device, which in turns leads to non-uniform coating.

Figure 5:
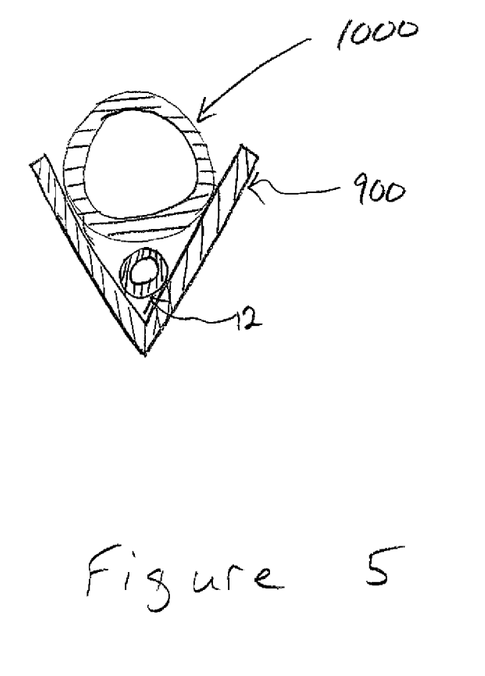
FIG. 5 is a schematic cross-sectional view of a support assembly for supporting the shaft of the catheter during a coating process.

During the coating process, the catheter shaft 12 can be positioned within a support assembly to counteract the circumferential and rotational forces and maintain the catheter shaft in a generally linear configuration. An example of such a support assembly is shown in FIG. 5, which includes a generally V-shaped structure 900 to define a channel for receiving the catheter shaft 12. A retaining rod 1000 is positioned above the shaft 12 and serves to obstruct or prevent the shaft 12 from being displaced out of the support assembly 900. In one embodiment, the retaining rod 1000 is configured with a cross-sectional dimension that limits the depth the retaining rod 1000 can be positioned within the V-shaped support assembly 900. Accordingly, the retaining rod 1000 is spaced from the shaft 12 to minimize contact, thereby minimizing the frictional forces generated during rotation of the shaft. Similarly, the support structure 900 can be coated with, or fabricated from, a lubricious material including Teflon, PEEK.

If desired, a protective sheath can be provided to protect the coating during shipping and storage and/or during delivery of the coated expandable member through the body lumen. A variety of sheaths are known, including removable sheaths or balloon covers, retractable sheaths to be withdrawn prior to deployment of the balloon, and elastic sheaths that conform to the balloon upon expansion. Such elastic sheaths can be porous or include apertures along a portion thereof. In operation, the inflation of the expandable member causes the sheath to expand for release of the coating and/or therapeutic agent through the porous wall or apertures to the tissue of the arterial wall. For example, see U.S. Pat. No. 5,370,614 to Amundson, the disclosure of which is incorporated by reference in its entirety.

In accordance with in the disclosed subject matter, an endoprosthesis, e.g. stent, can be mounted on the expandable member. The type of stent that can be used includes, but is not limited to, bare metal stent, drug eluting stent, bioabsorbable stent, balloon-expandable stent, self-expanding stent, pro-healing stent, and self-expanding vulnerable plaque implant. The expandable member can be coated independently of the stent or in conjunction with the stent coating process. The stent coating can contain the same or different therapeutic agents from the catheter or expandable member. However, the particular coating on the catheter or expandable member can have distinct release kinetics from the therapeutic coating on the stent. The coating applied to the expandable member can be allowed to dry prior to placement of the stent thereon.

Alternatively, the coating could not be allowed to dry or cure past a "tacky" state before the stent is positioned and/or crimped onto it. This would enable the adhesion of the coating on the expandable member to the inside of the prosthesis. This process increases the retention of the prosthesis onto the expandable member (acting as a prosthesis retention enhancer) thus reducing the chance that the stent will move on the expandable member during the torturous delivery through the vascular lumen While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of coating an inflatable balloon of a medical device, comprising:
   providing a dispenser in fluid communication with a fluid source, the dispenser having at least one outlet to dispense fluid of the fluid source therefrom;
   positioning the at least one outlet of the dispenser proximate a surface of an inflatable balloon;
   establishing relative movement between the at least one outlet and the surface of the inflatable balloon along a coating path;
   dispensing fluid from the dispenser to form a substantially continuous bead of fluid extending between the at least one outlet and the surface of the inflatable balloon and along the coating path; and
   simultaneously drying the fluid while dispensing the fluid from the dispenser to control flow of fluid on the surface of the inflatable balloon.

2. The method of claim 1, wherein the fluid remains substantially in a location where it contacts the surface of the inflatable balloon.

3. The method of claim 1, wherein relative movement provides a velocity ranges approximately from 2 to 20 cm/sec.

4. The method of claim 1, wherein the dispenser is selected from the group consisting of pipet, tubing, flexible tubing, hypotubes, dies, and ball-bearing dispense tubing.

5. The method of claim 1, wherein the dispenser does not contact the inflatable balloon.

6. The method of claim 1, wherein the fluid includes a therapeutic agent.

7. The method of claim 1, wherein the inflatable balloon is inflated to a pressure of approximately 0.1 to 8 atm prior to coating.

8. The method of claim 6, wherein a dose density of the therapeutic agent on the inflatable balloon is greater than 200 ug/cm$^2$.

9. The method of claim 1, wherein the relative movement includes rotation, translation, or a combination thereof, of at least one of the inflatable balloon and the at least one outlet.

10. The method of claim 9, wherein the relative movement includes rotation, axial translation, or a combination thereof, of the other of the inflatable balloon and the at least one outlet.

11. The method of claim 9, wherein the medical device further includes a shaft extending from the inflatable balloon, wherein during rotation and translation of the inflatable balloon, the shaft remains straight.

12. The method of claim 9, wherein the medical device further includes a shaft extending from the inflatable balloon, wherein during rotation and translation of the inflatable balloon, a rotation torque is applied to a proximal hub disposed on the shaft.

13. The method of claim 9, wherein the relative movement includes moving the inflatable balloon relative a first axis, and moving the at least one outlet relative a second axis.

14. The method of claim 9, wherein the relative movement defines a helical coating path of the at least one outlet relative to the inflatable balloon.

15. The method of claim 1, wherein dispensing fluid to the surface of the inflatable balloon is repeated along a plurality of coating paths.

16. The method of claim 15, wherein a first fluid is dispensed during a first coating path, and a second fluid is dispensed during a second coating path.

17. The method of claim 1, further comprising controlling dispensing to apply a substantially uniform coating of fluid to a predetermined area of the inflatable balloon.

18. The method of claim 1, wherein the at least one outlet is heated while dispensing fluid therefrom.

19. The method of claim 1, wherein the dispenser includes a plurality of outlets offset from each other.

20. A system for coating an inflatable balloon of a medical device, the system comprising:

a support structure to support an inflatable balloon of a medical device;

a dispenser in fluid communication with a fluid source, the dispenser having at least one outlet for dispensing fluid of the fluid source therefrom, the dispenser positioned with the at least one outlet proximate a surface of the inflatable balloon supported by the support structure;

a dryer proximate the dispenser to simultaneously dry the fluid while dispensing the fluid from the dispenser to control flow of fluid on the surface of the inflatable balloon; and a drive assembly to establish relative movement between the at least one outlet and the surface of the inflatable balloon to dispense fluid from the dispenser as a substantially continuous bead of fluid extending between the at least one outlet and the surface of the inflatable balloon and along a coating path.

* * * * *